(12) United States Patent
Bragaglia

(10) Patent No.: US 6,254,898 B1
(45) Date of Patent: Jul. 3, 2001

(54) NUTRACEUTICAL COMPOSITION FOR PROTECTION AGAINST SOLAR RADIATION

(75) Inventor: Anthony Joseph Bragaglia, Boston, MA (US)

(73) Assignee: Protective Factors, Inc., Boston, MA (US)

( * ) Notice: Subject to any disclaimer, the term of this patent is extended or adjusted under 35 U.S.C. 154(b) by 0 days.

(21) Appl. No.: 09/578,596

(22) Filed: May 25, 2000

(51) Int. Cl.[7] .............................. A61K 7/42; A61K 7/44; A61K 35/78; A61K 39/385; A01N 65/00

(52) U.S. Cl. ........................ 424/729; 424/59; 424/60; 424/195.1; 424/441; 424/445; 424/464; 424/725

(58) Field of Search .................... 424/195.1, 643, 424/441, 455, 464, 59, 60, 729, 725

(56) References Cited

U.S. PATENT DOCUMENTS

| | | | |
|---|---|---|---|
| 5,498,412 | * | 3/1996 | Fujie . |
| 5,527,552 | * | 6/1996 | Todd, Jr. . |
| 5,948,443 | * | 9/1999 | Riley et al. . |
| 5,976,568 | * | 11/1999 | Riley . |
| 6,096,359 | * | 8/2000 | Bombardelli et al. . |

FOREIGN PATENT DOCUMENTS

| | | | |
|---|---|---|---|
| 402096142A | * | 3/1990 | (JP) . |
| WO9422322 | * | 10/1994 | (WO) . |
| WO9628178 | * | 9/1996 | (WO) . |

OTHER PUBLICATIONS

No et al., Life Sciences, 65(21): pp PL 241–246, Inhibition of tyrosinase by green tea components, 1999.*

* cited by examiner

*Primary Examiner*—Christopher R. Tate
*Assistant Examiner*—Michele Flood
(74) *Attorney, Agent, or Firm*—Mueller and Smith, LPA

(57) ABSTRACT

A nutraceutical composition, for the inhibition of photochemical damage to the skin and eyes induced by sunlight, particularly by exposure to ultraviolet radiation is disclosed. The blend is multifunctional and comprises a blend of chemopreventive natural products, which exert anti-radical mechanisms of prevention and intervention, anti-inflammatory effects, enhance the endogenous defense mechanisms, and also have the potential to reduce the radiation induced pigmentation. The active ingredients in the blend include green tea extract, lutein (zeaxanthin), lipoic acid, and selenomethionine.

8 Claims, 2 Drawing Sheets

US 6,254,898 B1

NUTRACEUTICAL COMPOSITION FOR PROTECTION AGAINST SOLAR RADIATION

CROSS-REFERENCE TO RELATED APPLICATIONS

None

STATEMENT REGARDING FEDERALLY SPONSORED RESEARCH

Not applicable.

BACKGROUND OF THE INVENTION

1. Field of the Invention

The present invention relates to the development of a nutraceutical composition for the prevention and protection of photodamage to the skin and eyes resulting from solar or solar simulated radiation.

2. Related Art

Exposure of human skin to sunlight and, in particular, to the ultraviolet band of the spectrum, has many deleterious effects, including sunburn, erythema, photoallergic reactions, photoaging, hyperpigmentation, and the promotion of skin cancers. Sunlight induced non-melanoma skin cancer is a major cancer in the United States and in other temperate parts of the world. Solar radiation also has been suggested as one of the etiological factors in the development of degenerative diseases of the eyes, such as, age-related macular degeneration and cataract formation. Epidemiological studies have revealed a close correlation between photochemical damage and macular degeneration (Schalch, W., *EXS*, 62:280–98, 1992). Similarly, cataract formation is mainly due to changes in the lens proteins continually exposed to solar radiation (Varma, S. D., Chand, D., Sharma, Y. R., Kuck, J. F., and Richards, R. D., *Current Eye Res.*, 3:35, 1984). The risks of over-exposure to UV radiation will become greater with continued depletion of stratospheric ozone. The deleterious effects of ultraviolet radiation have been attributed largely to the generation of free radicals, such as superoxide and hydrogen peroxide.

As a result of concerns about the deleterious effects of over-exposure to sunlight, much research has been directed to the development of both topical and systemic photoprotective agents. Topical sunscreens or sunblockers physically block the sunlight from reaching the skin surface; some of them also may contain natural antioxidants and/or anti-inflammatory agents. Nutritional and pharmaceutical supplements, on the other hand, enhance the endogenous defense mechanisms at a cellular level, in addition to acting as antioxidants and anti-inflammatory agents. A number of formulations containing antioxidant vitamins, minerals, and herbal extracts either in the form of soft drinks, tablets for oral ingestion, or injections have been reported or patented (Pathak, M. A., "Topical and Systemic Photoprotection of Human Skin Against Solar Radiation", in H. W. Lim and N. A. Sotek, (eds.), *Clinical Photomedicine*, New York, Marcel Dekker, Inc. (1993); Pathak, et al, 1997; Wei, 1998; Shapira, 1998). However, none of the supplements address all the aspects of the afflictions caused by solar radiation.

More recently, U.S. Pat. No. 5,804,168 discloses a pharmaceutical composition consisting broadly of an antioxidant component comprising ascorbic acid, proanthocyanidins from grape seed, vitamin A, ginkgo biloba, and silymarin, an anti-inflammatory component, comprising zinc/vitamin E, an immune boosting component comprising echinacea and/or golden seal, in addition to β-carotene, minerals such as selenium, magnesium, and manganese, a cysteine component, and various herbs. The composition, however, does not address specific effects such as UV induced hyperpigmentation or damage to the eyes.

BRIEF SUMMARY OF THE INVENTION

A nutraceutical composition, for the inhibition of photochemical damage to the skin and eyes induced by sunlight, particularly by exposure to ultraviolet radiation is disclosed. The blend is multifunctional and comprises a blend of chemopreventive natural products, which exert anti-radical mechanisms of prevention and intervention, anti-inflammatory effects, enhance the endogenous defense mechanisms, and also have the potential to reduce the radiation induced pigmentation. The active ingredients in the blend include green tea extract, lutein (zeaxanthin), lipoic acid, and selenomethionine.

BRIEF DESCRIPTION OF THE DRAWINGS

The invention is better understood by reading the following Description of the Preferred Embodiments with reference to the accompanying drawing figures, in which like reference numerals refer to like elements throughout, and in which.

DESCRIPTION OF THE PREFERRED EMBODIMENTS

Figure 1:
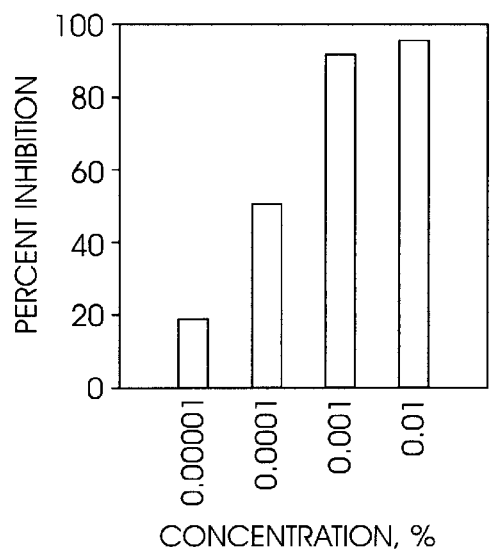
FIG. 1 is a bar graph showing the DPPH radical reduction by the Sunray blend as described in Example 1.

A nutraceutical composition containing natural products for protecting the skin and eyes from damage caused by exposure to solar radiation is disclosed. The formulation can be used both for prevention of sunlight damage and post exposure treatment. The principle components of the present invention are: green tea, lutein, lipoic acid, and selenomethionine. These ingredients function collectively to ameliorate the various deleterious effects of UV radiation. The mechanism of action of each component has been researched in animal experiments and human studies.

Oral feeding or topical application of green tea polyphenols has been reported to exert significant protection against ultraviolet B radiation induced sunburn lesion formation, erythema, tumor initiation, and tumor promotion in animal experiments (Agarwal, R., Katiyar, S. K., Khan, S. G., and Mukhthar, H., *Photochem. Photobiol.*, 58: 695–700, 1993; Wang, Z. Y., Agarval, R., Bickers, D. R., and Mukhtar, H., *Carcinigenesis*, 12: 1527–1530, 1991; Mukthar, H., Katiyar, S. K., and Agarwal, R., *J. Invest. Dermatol.*, 102: 3–7, 1994). In addition to a strong free radical quenching activity, green tea polyphenols inhibit the major biochemical markers for tumor initiation (cytochrome P-450 enzyme system) and tumor promotion (epidermal ornithine decarboxylase).

Ultraviolet radiation also upregulates the mRNA level for tyrosinase, the rate-limiting enzyme in melanin biosynthesis, which induces the hyperpigmentary disorders (Fuchs, J., Mehlhorn, R., and Packer, L., *J. Invest. Dermatol.*, 93: 633–640, 1989). In a recent study, No, et al. (No, J. K., Soung, D. Y., Kim, Y. J., Shim, K. H., Jun, Y. S., Rhee, S. H., Yokozawa, T., and Chung, H. Y., *Life Sciences*, 65: 241–246, 1999) have reported that green tea polyphenols inhibit tyrosinase, indicating a potential against prevention of the hyperpigmentation effects.

Lipoic acid (6,8-thioctic acid), an endogenous disulfide, is used in the treatment of liver diseases in which free radical induced lipid peroxidation appears to be involved. Lipoic acid has been shown to provide protection against free radical mediated lipid peroxidation and inflammation in vivo and in vitro (Fuchs, J., Milbradt, R., and Zimmer, G., *Free Radical Biol Med.*, 9: 189, 1990; Bast, A. and Haenen, G. R. M. M., *Biochim. Biophys. Acta*, 963: 558–561, 1988). Ramakrishnan, et al. (Ramakrishnan, N., Wolfe, W. W., and Catravas, G. N., *Radiation Res.*, 130: 36–365, 1992) have reported that lipoic acid has a protective effect against radiation injury to hematopoietic tissues in mice. Lipoic acid has also been reported to have a protective effect against eye lens damage (Kilic, F., Handleman, G. J., Serbinova, E., Packer, L., and Trevithick, J. R., *Biochem., Mol. Biol. Int.*, 37: 361–370, 1995).

Lutein is a potent free radical quencher and also is highly effective in the prevention and treatment of macular degeneration and lowers the risk of cataract formation. Structural and clinical studies have shown that lutein and zeaxanthin are concentrated in the retinal macular pigment and that such accumulation is dependent on dietary intake (Schalch, W., *EXS*, 62:280–98, 1992). Animal experiments and epidemiological studies have indicated a protective role of lutein and zeaxanthin in the retina (Pratt S, *J Am Optom Assoc.*, 70: 39–47, 1999). Epidemiological studies also have indicated that intake of spinach (rich in lutein and zeaxanthin) was consistently associated with a lower relative risk of developing cataracts rather than consumption of carrots (high in β-carotene) (Hankinson, S. E., Stampfer, M. J., Seddon, J. M., Colditz, G. A., Rosner, B., Speizer, F. E., and Willett, W. C., *British Med. J.*, 305: 335–339, 1997).

Selenium is essential for the detoxifying activity of the endogenous antiradical defense systems, such as Se-dependent glutathione peroxidase. In animal studies, oral supplementation or topical application of selenium delayed the appearance the skin tumors, reduced lipid peroxidation, inflammation, and pigmentation caused by UV radiation (Burke, K. E., Combs, G. F., Gross, E. G., Bhuyan, K. C., and Abu-libdeh, H., *Nutr. Cancer*, 17: 123–137, 1992). Human studies have indicated a strong inverse association between plasma selenium levels and non-melanoma skin cancer (Clark, L. C., Graham, G. F., Crounse, R. G., Grimson, R., Hulka, B., and Shy, C. M., *Nutr. Cancer*, 6:13–21, 1984).

In a preferred embodiment, the composition contains green tea polyphenols as one of the components in about 0.05 to 50 weight percent, wherein the polyphenol content is between 30 to 50 weight percent. Lipoic acid is present in about 0.01 to 10 weight percent of the formulation. Selenomethionine is present at about 0.00001–0.01 weight percent. Lutein is present at about 0.00015–0.15 weight percent, and contains at least 1–2% by weight of zeaxanthin.

While the invention has been described in detail with particular reference to these principle active ingredients, numerous modifications and substitutions can be used to alter the weight percent of the components, incorporate additional bioactive components from natural sources, and to develop more effective, novel molecular complexes combining active ingredients from different sources.

The invention further includes incorporation of the active ingredients into two-piece hard gelatin capsules at about a 150–400 mg level. The capsule includes a natural inert carrier, such as, for example, rice flour at about 37 weight percent, and is suitable for oral administration in discrete units. The composition also is suitable for incorporation into soft gelatin capsules or tablets, each containing a predetermined amount of the active ingredients, for example, as a powder, granules, or a suspension in edible oils.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

EXAMPLES

Example 1

Quenching of Free Radicals

The cytotoxic effects of ultraviolet A irradiation on mammalian cells (e.g., skin fibroblasts) have been attributed largely to photoreactions that generate reactive oxygen species, such as superoxide and hydrogen peroxide. The free radical scavenging activity of the blend and its components was determined in vitro using spectrophotometric assays (Yen, G. C. and Duh, P. D., *J. Agric. Food Chem.*, 42: 629–632, 1994; Facino, R. M., Carini, M., Aldini, G., Berti, F., and Rossoni, G., *Planta Med.*, 65: 614–619, 1999). The superoxide scavenging activity was assessed in a non-enzymatic system. The reduction of the stable free radical DPPH (2,2-diphenyl-1-picrylhydrazyl radical), indicative of the neutralizing action upon the already formed free radicals, also was determined in a cell-free system.

Material and Methods

Materials

Phenazine methosulfate, β-NADH, Nitroblue tetrazolium, and DPPH were purchased from Sigma (Sigma-Aldrich, Inc., St. Louis, Mo.). The inventive blend and its components were supplied in a capsule containing: green tea extract, 250 mg; lutein, 15 mg; Se, 50 mcg; and lipoic acid, 50 mg. The capsule's contents were extracted in ethanol [0.5 g (contents of one capsule) in 5 ml ethanol and the components at concentrations incorporated in the blend in 5 ml ethanol].

Methods

The superoxide scavenging activity was determined in a superoxide generating system containing 20 $\mu$M of phenazine methosulfate, 156 $\mu$M of β-NADH, 50 mM of phosphate buffer, and the extracts at various levels. The reaction was initiated by adding nitroblue tetrazolium (25 $\mu$M) and the reduction was monitored using a spectrophotometer at 556 nm. For the determination of the reduction of DPPH radical, DPPH was used at a concentration of 0.02% in methanol. Various concentrations of the extracts in ethanol were added and the mixture was incubated at 25° C. for 1 min. The reduction in absorbence was measured using a spectrophotometer at 515 nm. The results are the means ±SD of triplicate measurements. The percent inhibition is expressed as the quenching ratio represented by the following formula:

$$\text{Inhibition}(\%) = \frac{(A-B)}{A \times 100},$$

Where:
A is the absorption of the reference solution, and
B is the absorption of the test solution.
Observations The DPPH reducing activity of the blend is presented in Table 1 and FIG. 1.

TABLE 1

DPPH Radical Reduction

| Concentration (%) | Inhibition (%) |
|---|---|
| 0.01 | 95.64 ± 0.15 |
| 0.001 | 92.6 ± 0.66 |
| 0.0001 | 50.3 ± 1.31 |
| 0.00001 | 19.1 ± 0.07 |

The blend showed a potent scavenging ability over a concentration range of 0.00001–10% and a 50% quenching was observed at 25 $\mu$g concentration. Of the four components, green tea extract and lutein were the most active at the dilutions tested. The concentration required for 50% quenching was 12.5 $\mu$g for green tea extract and 450 $\mu$g for lutein.

Figure 2:
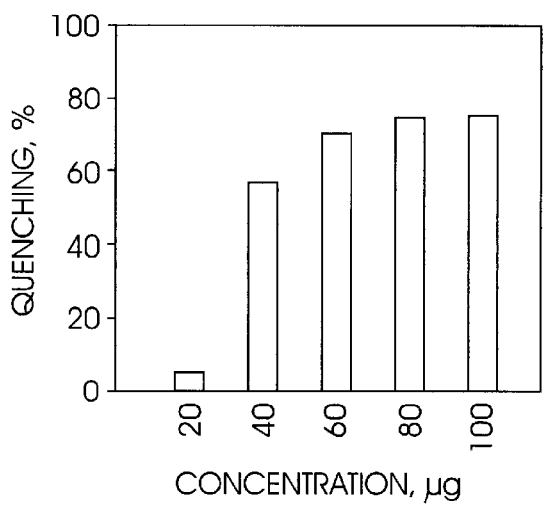
FIG. 2 is a bar graph showing the superoxide quenching activity of the Sunray blend as described in Example 1.

The blend also showed a strong superoxide quenching ability over a concentration range of 0.00001–10% (FIG. 2). The effect was dose dependent, with a 50% quenching at 30 $\mu$g. Of the four components, green tea and lipoic acid were found to be most active at the dilutions tested. The concentration required for 50% quenching was 20 $\mu$g for green tea extract and 7.5 mg for lipoic acid.

Example 2

Serine Protease Inhibitory Activity

Exposure to solar radiation, especially to ultraviolet A radiation, is reported to cause short-term inflammatory skin conditions, such as burning, erythema, and itching; while the long-term effects could lead to actinic dermatitis and carcinogenesis. Serine proteases, including elastase, trypsin and, cathepsin G, play an important role in the tissue damage leading to inflammation. Serine protease inhibitors have been found to play a major role in the direct inactivation of the mediators of inflammation and accelerate the healing process. The use of serine protease inhibitors appears to be a viable alternative to the administration of steroids to treat inflammatory skin conditions or to reduce the steroid requirement (Lezdey, J. and Wachter, A. J., U.S. Pat. No. 5,217,951).

Serine protease inhibitory activity was determined in vitro by measuring the trypsin inhibitory activity of the blend and its components. Trypsin inhibitory activity was determined by the spectrophotometric determination of the release of p-nitroaniline from a synthetic substrate N-$\alpha$-benzoyl-DL-arginine-p-nitroanilide hydrochloride (BAPNA) (Parellada, J. and Guinea, M., *J. Nat. Prod.*, 58: 823–829, 1995; Geiger, R. and Fritz, H., In *Methods of Enzymatic Analysis*, Bergmeyer, H. V., et al (Eds), Verlag-Chemie, Basel, Switzerland, Vol. V, p. 119–129, 1984).

Materials and Methods

Materials

Trypsin Type III from bovine pancreas, BAPNA, and p-nitroaniline were obtained from Sigma. The inventive blend and its components were supplied in a capsule containing: green tea extract, 250 mg; lutein, 15 mg; Se, 50 mcg; and lipoic acid, 50 mg. The capsule's contents were extracted in ethanol [0.5 g (contents of one capsule) in 5 ml ethanol and the components at concentrations incorporated in the blend in 5 ml ethanol].

Methods

Aliquots of the enzyme solution (0.25 ml of a 1060 units/ml solution in 0.05 M Tris buffer, pH 7.8) and the buffer (0.25 ml) with various concentrations of the test extracts and without extracts (reference solution) were pre-incubated at 37° C. for 10 min. Blank samples were prepared by inactivating the enzyme with 0.5 ml of 2 M acetic acid before incubation. The enzymatic reaction was started by adding to the reaction mixture 1.25 ml of the substrate solution (1 mM in 0.05 M Tris buffer, pH 7.8). The mixture was incubated for 10 min and the reaction was stopped by adding 0.5 ml of 2 M acetic acid. The p-nitroaniline released was measured using a spectrophotometer at 410 nm. The results are the means ±SD of triplicate measurements. The inhibitory activity is expressed as the inhibition ratio represented by the following formula:

$$\text{Inhibition ratio }(\%) = \frac{[(A-B)-(D-C)]}{(A-B) \times 100},$$

where:
A is the absorption of the reference solution,
B is the absorption of the reference solution blank,
C is the absorption of the test solution, and
D is the absorption of the test solution blank.

Observations

The superoxide quenching activity of the blend is presented in Table 2 and FIG. 2.

TABLE 2

Superoxide Quenching

| Concentration ($\mu$g) | Quenching (%) |
|---|---|
| 20 | 4.54 ± 0.92 |
| 40 | 57.63 |
| 60 | 71.98 ± 7.95 |
| 80 | 76.34 ± 5.72 |
| 100 | 76.39 ± 3.53 |

Figure 3:
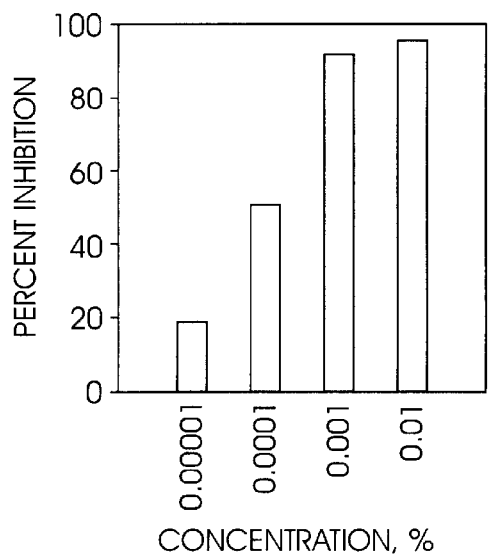
FIG. 3 is a bar graph showing the trypsin inhibitory activity of the Sunray blend as described in Example 2.

The trypsin inhibitory activity of the blend is presented in Table 3 and FIG. 3.

TABLE 3

Trypsin Inhibitory Activity

| Concentration, % | Percent Inhibition |
|---|---|
| 0.01 | 83.13 ± 0.89 |
| 0.001 | 59.58 ± 2.02 |
| 0.0001 | 24.11 ± 4.13 |
| 0.00001 | 16.97 ± 5.17 |

The inventive blend showed a potent trypsin inhibitory activity over the concentration range of 0.01–0.00001%, and the $IC_{50}$ was 0.175 mg (FIG. 3). All the components were active in the assay at the dilutions tested for the blend, and the $IC_{50}$ for each component was: green tea extract, 0.625 mg; lutein, 0.135 mg; lipoic, acid 0.1 mg; and selenium, 0.015 µg.

Example 3

Inhibition of Tyrosinase Activity

Although melanin is a major defense mechanism against ultraviolet radiation, production of abnormal pigmentation, such as melasma, freckles, and other forms of hyperpigmentation, could be a serious aesthetic problem (Priestly, G. C., (Ed), *Molecular Aspects of Dermatology*, John Wiley & Sons, United Kingdom, 1993). Modulation of melanin synthesis can prevent or cure the hyperpigmentary disorders. The tyrosinase inhibitory effects of the blend and its components were determined in vitro in a spectrophotometric assay (No, J. K., Soung, D. Y., Kim, Y. J., Shim, K. H., Jun, Y. S., Rhee, S. H., Yokozawa, T., and Chung, H. Y., *Life Sciences*, 65: 241–246, 1999).

Materials and Methods

Materials

Mushroom tyrosinase and L-tyrosine were purchased from Sigma. The inventive blend and its components were supplied in a capsule containing: green tea extract, 250 mg; lutein, 15 mg; Se, 50 mcg; and lipoic acid, 50 mg. The capsule's contents were extracted in ethanol [0.5 g (contents of one capsule) in 5 ml ethanol and the components at concentrations incorporated in the blend in 5 ml ethanol].

Methods

The assay mixture contained 1 mM L-tyrosine, 50 mM potassium phosphate buffer at pH 6.5, 100 units of tyrosinase, and various concentrations of the extracts diluted in the buffer in a total volume of 1.5 ml. The mixture was incubated at 25° C. for 30 min and the amount of dopachrome produced was determined using a spectrophotometer at 492 nm. The results are the means ±SD of triplicate measurements. The inhibitory activity is expressed as the inhibition ratio represented by the following formula:

$$\text{Inhibition}(\%) = \frac{(A - B)}{A \times 100},$$

where:
A is the absorption of the reference solution, and
B is the absorption of the test solution.

Observations

Figure 4:
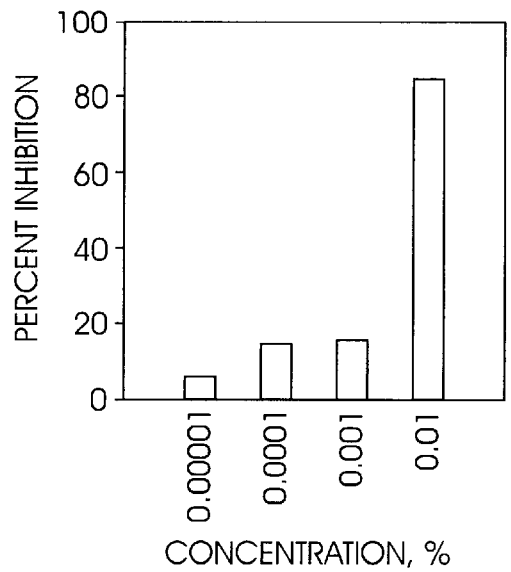
FIG. 4 is a bar graph showing the tyrosinase inhibitory activity of the Sunray blend as described in Example 3.

The tyrosinase inhibitory activity of the blend is presented in Table 4 and FIG. 4.

TABLE 4

Tyrosinase Inhibitory Activity

| Concentration (%) | Inhibition (%) |
|---|---|
| 0.01 | 83.54 ± 1.85 |
| 0.001 | 16.61 ± 2.8 |
| 0.0001 | 14.81 ± 0.91 |
| 0.00001 | 5.71 ± 2.9 |

The inventive blend showed a strong tyrosinase inhibitory activity at 0.01–0.001% concentration levels and the $IC_{50}$ was 1.4 mg (FIG. 4). Of the four components, green tea extract was the most active in the assay and the $IC_{50}$ was 0.625 mg.

Example 4

UV Protective Properties of the Blend

Exposure of skin to sunlight especially to ultraviolet A (320–380 nm) radiation has been reported to induce photochemical generation of reactive oxygen species, resulting in membrane lipid peroxidation, photodamage to DNA, and inactivation of fibroblasts. The long-term effects leading to skin aging and cancer have been demonstrated. A mammalian fibroblast cell line was used to determine the UV-protective action of the blend and the components at a cellular level. The testing procedure was developed based on the references (Morlier, P., Moysan, A., Santus, R., Huppe, G., Maziere, J., and Dubertret, L., *Biochim. Biophys. Acta*, 1084: 261–268, 1991; and Leccia, M. T., Richard, M. J., Beani, J. C., Faure, H., Monjo, A. M., Cadet, J., Amblard, P., and Favier, A., *Photochem. Photobiol.*, 58: 548–553, 1993).

Materials and Methods

Materials

A fibroblast cell line BALB/3T3 clone A31 (BALB/c embryo, mouse) obtained from ATCC (ATCC CCL-163) was used for the assay. UVP XX-15L Blackray lamp, with long wave UV bulbs (peak at 365 nm, 1.97 mW/cm$^2$, UVP, CA) was used as the radiation source. Dulbecco's Modified Eagle Medium (DMEM) with 4 mM L-glutamine and 110 mg/l sodium pyruvate, Dulbecco's phosphate buffered saline (DPBS) without calcium or magnesium, fetal bovine serum, trypsin-EDTA solution, 2-thiobarbituric acid, MTT, and trichloroacetic acid were obtained from Sigma. The inventive blend and its components were supplied in a capsule containing: green tea extract, 250 mg; lutein, 15 mg; Se, 50 mcg; and lipoic acid, 50 mg. The capsule's contents were extracted in ethanol [0.5 g (contents of one capsule) in 5 ml ethanol and the components at concentrations incorporated in the blend in 5 ml ethanol]. The extracts were diluted using the culture medium or DPBS.

Methods

1. Cultural Conditions

Cells were maintained in 250 ml Corning flasks having a 0.2 µ vented cap in 10 ml of DMEM supplemented with 10% fetal bovine serum. The cultures were incubated at 37° C. in a $CO_2$ incubator with 90% air and 10% $CO_2$. The cells were subcultured every 5 days.

2. Testing Procedure

Assays were performed in 35 mm Costar tissue culture plates. The cells were plated at a density of 90,000 cells per well in the growth medium and allowed to attach and grow for 48 hr. The medium was changed after 36 hr with fresh medium containing the extracts at different concentrations. After 12 hr of incubation with the test extracts, the cells were washed with DPBS to remove the original medium. One ml of DPBS with or without the test extracts was added to each dish. The cells were incubated for 1 hr before exposure to UV irradiation. Non-irradiated cells were used as the control. The irradiated and control cells were incubated in the medium for 18 hr and the viability was determined using the MTT assay (McHale, A. P. and McHale, L., *Cancer Letters*, 41: 315–321, 1988; and Hirano, T., Gotoh, M., and Oka, K., *Life Sciences*, 55: 1061–1069, 1994). Lipid peroxidation was determined in the cell lysates using the 2-thiobarbituric acid method of measuring malondialdehyde levels (Morlier, P., Moysan, A., Santus, R., Huppe, G., Maziere, J., and Dubertret, L., *Biochim. Biophys. Acta*, 1084: 261–268, 1991). The results are the means ±SD of triplicate measurements.

Observations

Figure 5:
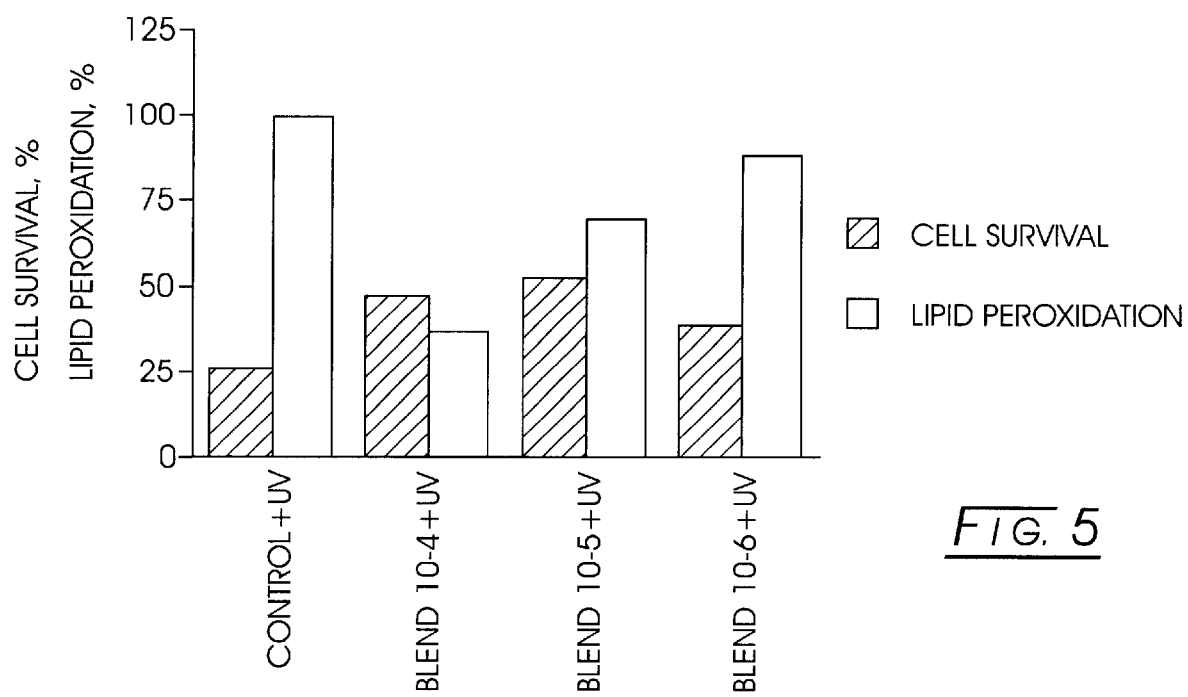
FIG. 5 is a bar graph showing the UV protecting activity of the Sunray blend at a cellular level as described in Example 4.

The UV protecting activity of the blend is presented in Table 5 and FIG. 5.

TABLE 5

UV Protecting Activity

| Concentration (%) | Cell Survival (%) | Lipid Peroxidation (%) |
|---|---|---|
| Control + UV | 26.08 ± 1.54 | 100 |
| Blend $10^{-4}$ + UV | 47.44 ± 0.23 | 36.84 ± 10.04 |
| Blend $10^{-5}$ + UV | 52.35 ± 5.05 | 69.48 ± 2.1 |
| Blend $10^{-6}$ + UV | 37.88 ± 1.58 | 88.07 ± 2.78 |

UVA irradiation reduced the viability of the cells to 26% of the untreated control. Treatment with the inventive blend extract increased the cell viability at the concentrations tested and nearly 50% viability was observed at 0.00001% concentration. The TBARS values, a marker of UV induced lipid peroxidation, also were reduced in the treated cells, and up to 69% reduction was observed at 0.00001% concentration. All the components were active in the assay, and the range of concentrations were: green tea extract, 0.000005–5 mg/ml; selenium, 0.001–1 µg/ml; lutein, 0.15 µg–15 µg/ml; and lipoic acid, 0.001–1 mg/ml.

What is claimed is:

1. A nutraceutical blend for the protection of photodamage induced by solar radiation, the active ingredients consisting essentially of a blend of:
   (a) green tea extract that contains polyphenols, said green tea extract content being between about 0.05 and 50 weight percent and the polyphenol content in said green tea extract is between 30 and 50 weight percent;
   (b) lipoic acid in an amount of between about 0.01 and 10 weight percent;
   (c) selenomethionine in an amount of between about 0.00001 and 0.01 weight percent; and
   (d) lutein content is between about 0.00015–0.15 weight percent.

2. The nutraceutical blend of claim 1, wherein said lutein also contains at least about 1–2% by weight of zeaxanthin.

3. The nutraceutical blend of claim 2, which is disposed in a capsule at a dosage of between about 150 and 400 mg.

4. A method for protecting against photodamage induced by solar radiation, which comprises:

administering to a person the nutraceutical blend of claim 1.

5. The method of claim 4, wherein said blend is administered orally at a dosage of between about 500 and 1000 mg.

6. A method for protecting against photodamage induced by solar radiation, which comprises:

administering to a person the nutraceutical blend of claim 2.

7. The method of claim 6, wherein said blend is administered orally at a dosage of between about 500 and 1000 mg.

8. A nutraceutical blend that has antioxidant, anti-inflammatory properties and inhibits tyrosinase activity, the active ingredients consisting essentially of:
   (a) green tea extract that contains polyphenols, said green tea extract content being between about 0.05 and 50 weight percent and the polyphenol content in said green tea extract is between 30 and 50 weight percent;
   (b) lipoic acid in an amount of between about 0.01 and 10 weight percent;
   (c) selenomethionine in an amount of between about 0.00001 and 0.01 weight percent; and
   (d) lutein content is between about 0.00015–0.15 weight percent, wherein said lutein also contains at least about 1–2% by weight of zeaxanthin.

* * * * *